(12) United States Patent
Kim

(10) Patent No.: US 8,911,404 B2
(45) Date of Patent: Dec. 16, 2014

(54) DELIVERY APPARATUS FOR MEDICAL FLUID IN BOX TYPE WITH A SYRINGE

(75) Inventor: Jung Hyun Kim, Kimpo (KR)

(73) Assignee: Jung Hyun Kim, Kimpo (KR)

( * ) Notice: Subject to any disclaimer, the term of this patent is extended or adjusted under 35 U.S.C. 154(b) by 1074 days.

(21) Appl. No.: 12/445,720

(22) PCT Filed: Oct. 22, 2007

(86) PCT No.: PCT/KR2007/005174
§ 371 (c)(1),
(2), (4) Date: Apr. 15, 2009

(87) PCT Pub. No.: WO2008/050977
PCT Pub. Date: May 2, 2008

(65) Prior Publication Data
US 2010/0191187 A1    Jul. 29, 2010

(30) Foreign Application Priority Data

Oct. 23, 2006  (KR) .......................... 10-2006-0103094

(51) Int. Cl.
*A61M 37/00* (2006.01)
*A61M 5/142* (2006.01)
*A61M 5/145* (2006.01)

(52) U.S. Cl.
CPC ....... *A61M 5/14244* (2013.01); *A61M 5/14566* (2013.01); *A61M 2205/502* (2013.01); *A61M 2005/14264* (2013.01)
USPC ........................................................ 604/154

(58) Field of Classification Search
CPC ................. A61M 2205/502; A61M 2205/505; A61M 5/142; A61M 5/14244; A61M 5/14566; A61M 2005/3152; A61M 5/31558
USPC ....................... 604/131, 151–155; 128/DIG. 1
See application file for complete search history.

(56) References Cited

U.S. PATENT DOCUMENTS

| 2002/0011580 A1 | 1/2002 | Johansen et al. | |
| 2003/0009133 A1* | 1/2003 | Ramey | 604/155 |
| 2003/0163090 A1* | 8/2003 | Blomquist et al. | 604/154 |

FOREIGN PATENT DOCUMENTS

| KR | 10-1999-0014521 A | 4/1999 |
| KR | 10-2004-0084214 A | 10/2004 |

* cited by examiner

*Primary Examiner* — Matthew F DeSanto
(74) *Attorney, Agent, or Firm* — Jefferson IP Law, LLP

(57) ABSTRACT

Disclosed is a delivery apparatus for medical fluid, in which a body is fabricated in a box shape and a cover is detachably coupled to the body, thereby facilitating the repairing work for the delicate malfunction of the apparatus and a fluctuation-prevention member is provided such that a syringe makes a vertical movement after the installation of the syringe even if the body is fabricated in the box shape.

7 Claims, 4 Drawing Sheets

Fig. 6
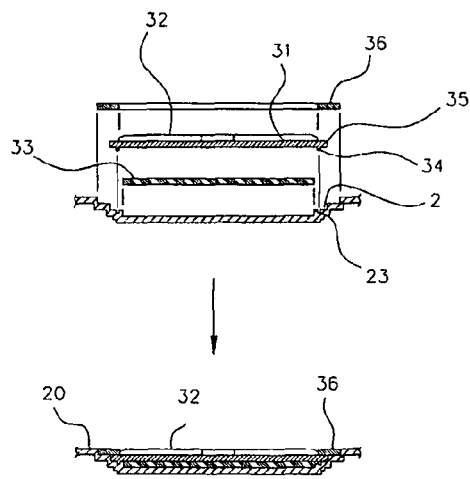
Fig. 7
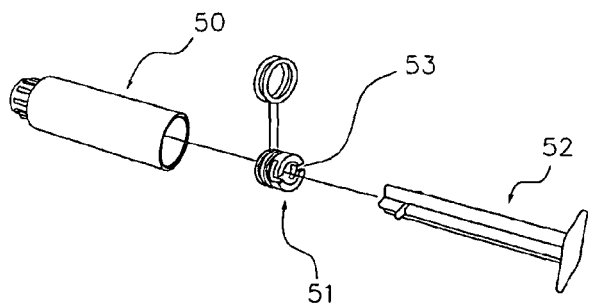
[Fig. 8]
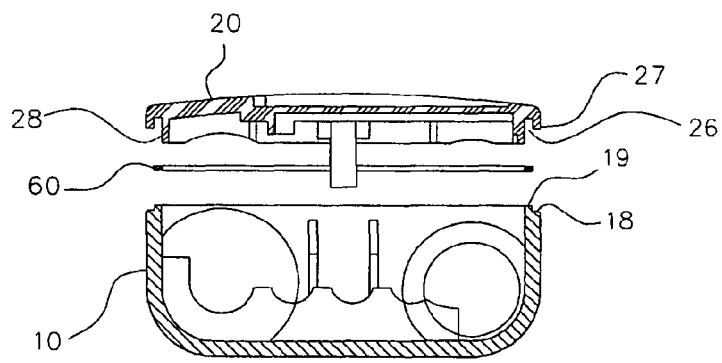
Fig. 9
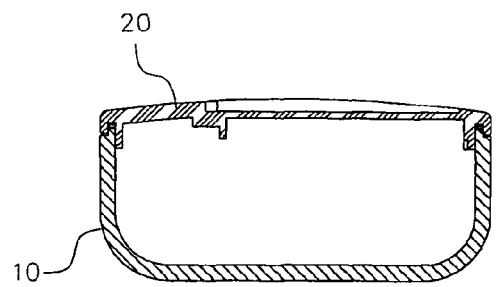

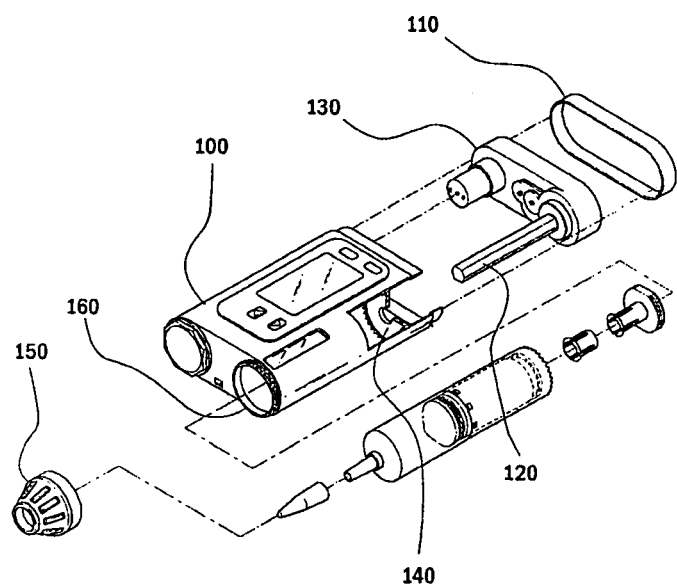

DELIVERY APPARATUS FOR MEDICAL FLUID IN BOX TYPE WITH A SYRINGE

TECHNICAL FIELD

The present invention relates to an automatic portable medical fluid injector used for diabetic patients. More particularly, the present invention relates to an automatic portable medical fluid injector, in which assemble/disassemble of an injection device is easy performed with superior airtight function, a syringe is detachably installed and operational accuracy is improved.

BACKGROUND ART

Currently, a portable medical fluid injector is used to inject medical fluid into a diabetic patient using a syringe. In order to periodically inject insulin into the diabetic patient, the injector is automatically operated at a predetermined time interval in a state in which a syringe is pierced into a pancreas of the diabetic patient, thereby controlling blood sugar level of the diabetic patient.

However, the injector must be kept on a human body, so a waterproof function and operational stability are required to precisely inject the medical fluid.

To this end, a case of the injector has a body 100 having a tube shape, in which top and bottom sections of the body 100 are open. The bottom section of the body 100 is covered with a cover 110, thereby ensuring waterproof function and inducing operation of a movable shaft used for injecting medical fluid.

However, the cover 110 that covers the bottom section of the body 100 having the tube shape is permanently fixed to the bottom section, so that repairing the injector is difficult when the injector is broken.

In addition, the movable shaft 120 that induces operation of a syringe, which is installed in the body and is filled with insulin, is supported by the cover 110 at a lower portion of the body having the tube shape. However, such a cover 110 has a small coupling section so that the cover 110 cannot ensure the fixation of a power supply unit 130 that operates the movable shaft 120. Thus, the movable shaft may be shaken when injecting the medical fluid, so that the medical fluid cannot be precisely injected into the diabetic patient.

For this reason, an additional fixing member 140 must be prepared in the body 100 to fix the movable shaft, causing a difficult in fabricating the body 100.

In addition, after the syringe is inserted into the automatic injector, in order to prevent water from flowing into the body or prevent the syringe from being separated from the body, a cap 150 is screw-coupled to the case through a fastening portion 160. However, this structure causes breakage or crack on the body 100. Therefore, a repairing process is necessary.

DISCLOSURE OF INVENTION

Technical Problem

According to the present invention, there is provided a delevery appartus for medical fluid, in which a case can be disassembled while maintaining the waterproof function when breakage or malfunction occurs, predetermined pressure is applied to a cover after a syringe is installed, a movable shaft can be precisely moved up and down to accurately feed medical fluid, and a stopper for a gear box driven by a motor that induces the up/down movement of the movable shaft is provided.

Technical Solution

The apparatus for injecting medical fluid comprises a case including a body, which is open at an upper portion thereof, and a cover which is coupled with the body through two-step engagement, in which a packing is pressed when the cover is coupled with the body to ensure the airtight function. A stopper is provided in the body and an engagement part, which is engaged with the stopper, is formed in the gear box such that the gear box is securely fixed to the body. The up/down movement of a movable shaft can be accurately performed by means of a guide wing. In the case of a cap for a portion, through which a syringe is detachably installed, a guide protrusion formed on the cap is engaged with an inclined groove formed on the body, so that the cap may rotate while being pressed. In this case, a stopper enables the cap to be pressed at a pre-determined level of pressing force, thereby preventing breakage of the case, facilitating the repairing work upon the breakage of the injector and ensuring the precise operation of the injector.

Advantageous Effects

According to the present invention, a cover constituting a case opens/closes an open upper surface of a body, thereby facilitating repairing work and assembling work and ensuring a secure fixation of a gear box. In addition, a movable shaft is inserted into a cylinder such that the movable shaft can be precisely move up and down, so that medical fluid can be precisely injected into the patient.

BRIEF DESCRIPTION OF THE DRAWINGS

FIG. 6 is a sectional view representing the mounting state of the keypad part for the waterproof function according to the present invention;

FIG. 7 is an exploded perspective view representing the syringe installed on the body according to an embodiment of the present invention;

FIG. 8 is a sectional view representing the body of a case and a cover separated from each other according to the present invention;

FIG. 9 is a sectional view representing the body of the case and the cover assembled with each other according to the present invention; and FIG. 10 is an assembled view representing an automatic injector according to the related art.

DESCRIPTION OF NUMERALS FOR IMPORTANT PARTS OF THE DRAWINGS

Figure 1:
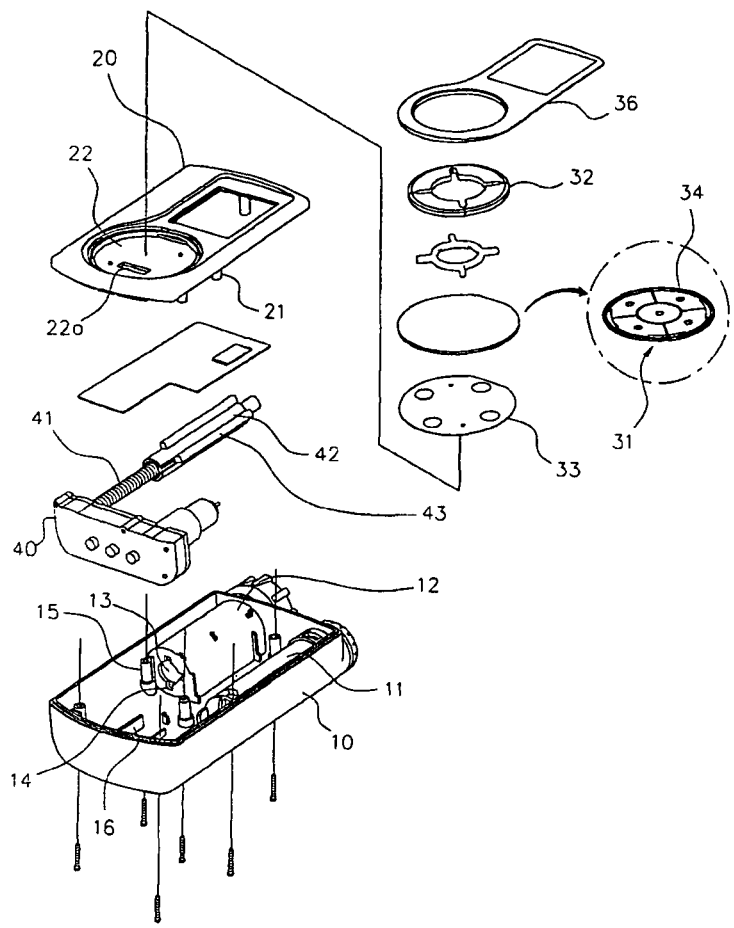
FIG. 1 is an exploded perspective view representing an entire structure of an apparatus for injecting medical fluid according to the present invention.

10: body 11: battery receptacle
12: syringe receptacle 13: perforation part
14: guide groove 15: coupling protrusion
16: supporting guide 17: stopper 18: protrusion 19: protruding rim
20: cover 21: coupling protrusion
22: recess 23: recess rim
24: support surface 25: window section
26: packing groove rim 27: outer rim
28: inner rim
30: key pad 31: rubber pad
32: pressing part 33: substrate
34: protruding rim 35: flange
36: cover plate
40: gear box 41: rotating shaft
42: movable shaft 43: guide wing
44: engagement part
50: cylinder 51: packing part
52: piston 53: embedded part
71: guide protrusion 72: packing

BEST MODE FOR CARRYING OUT THE INVENTION

Hereinafter, the most preferred embodiment of the present invention will be described in detail with reference to the accompanying drawings. The same elements may have the same reference numerals even if they are shown in different drawings.

Figure 2:
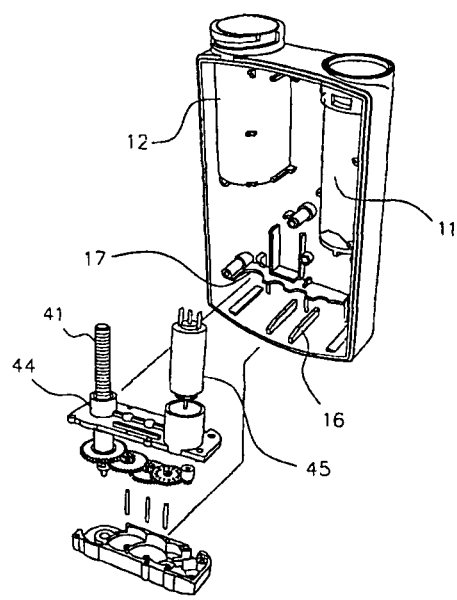
FIG. 2 is an exploded perspective view representing a gear box assembled to a body according to the present invention.
Figure 3:
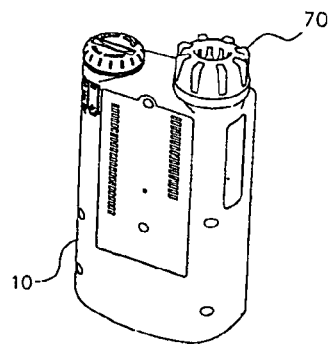
FIG. 3 is an assembled perspective view of the apparatus for injecting medical fluid according to the present invention.
Figure 4:
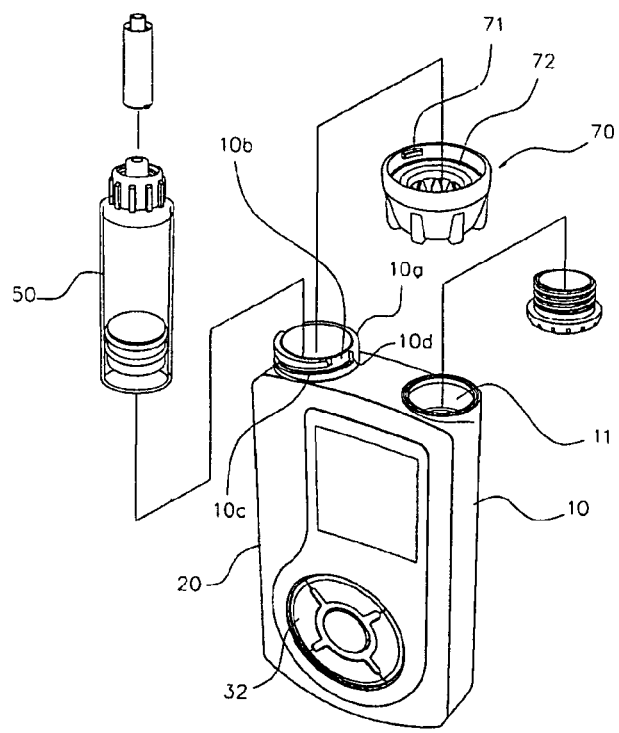
FIG. 4 is an exploded perspective view representing a syringe and a cap according to the present invention.
Figure 5:
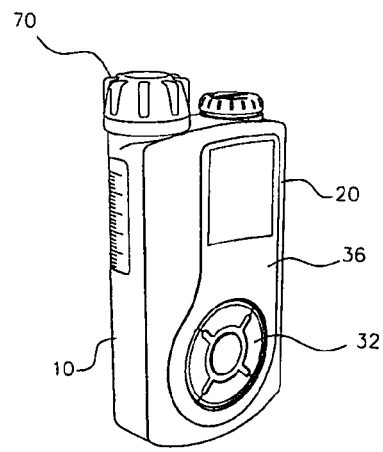
FIG. 5 is a perspective view representing a keypad part in a state in which the apparatus for injecting medical fluid is assembled according to the present invention.

As shown in FIGS. 1 to 5, a delivery apparatus for medical fluid fabricated in a box type with a syringe according to the present invention is provided with a case. The case includes a body 10, an upper portion of which is open and in which a battery receptacle 11 and a syringe receptacle 12 are integrally formed. A movable shaft 42, which is rotatably engaged with a rotating shaft 41 installed in a gear box 40 driven by a motor 45, is introduced into and withdrawn from a syringe receptacle 12. A keypad 30 for controlling an operation of the movable shaft 42 is installed in a recess 22 of a cover 20 and is fixed by a pressing part 32 and a cover plate 36. Accordingly, the cover 20 and the body 10 are screw-fastened in a state in which coupling protrusions 15 and 21 thereof are engaged with each other such that the cover 20 is detachably coupled to the body 10.

A stopper 17 is formed at a lower portion of the body 10 forming the case such that the stopper 17 is engaged with an engagement part 44 of the gear box 40 having the movable shaft 42 which allows a packing part 51 installed on a cylinder 50 of the syringe, which is housed in the syringe receptacle 12, to precisely perform a vertical movement. Therefore, the movable shaft 42 is prevented from being fluctuated when the motor 45 operates and when the rotating shaft 41 protruding through the engagement part 44 rotates.

In this case, the rotating shaft 41 is integrally connected with a gear embedded in the gear box 40, thereby obtaining a driving force. The engagement part 44 has an inner diameter, which is larger than an outer diameter of the rotating shaft 41 to prevent collision with the rotating shaft 41.

In addition, the movable shaft 42 having a guide wing 43 installed thereon is screw-coupled to the rotating shaft 41, so that the movable shaft 42 is engaged with a perforation part 13 and a guide groove 14 of the syringe receptacle 12 when the rotating shaft 41 rotates, thereby enabling the movable shaft 42 to make a precise vertical movement.

Accordingly, the movable shaft 42 is inserted into the cylinder 50 of the syringe and the guide wing 43 of the movable shaft 42 is coupled to an embedded part 53 of the packing part 51, so that the movable shaft 42 is prevented from being fluctuated and only the packing part 51 positioned in the cylinder 50 moves upward/downward, thereby preventing the cylinder 50 from moving left/right directions. As a result, the movable shaft 42 makes a precise vertical movement, so that exact dose of medical fluid can be injected.

In addition, the gear box 4 closely comes into contact with the body 10. In order to prevent vibration occurring due to a rotation of the motor 45 from being transferred into the movable shaft 42, a supporting guide 16 is formed on the body 10 making a contact with the gear box 40, so that a gap is maintained between the gear box 40 and the body 10, thereby absorbing the vibration.

In order to perform a waterproof treatment relative to a key pad 30 for operating the motor 45 of the gear box 40, a recess 22 is formed in the cover 20 such that the recess 22 has a predetermined depth enough to receive the key pad 30. A connecting hole 22a is formed in the recess 22 for signal connection with the substrate 33 of the key pad 30. A protruding rim 34 having a flange 35 is formed at an edge of the rubber pad 31 covering the substrate 33 received in the recess 22. In addition, a recess rim 23 and a support surface 24 are formed on an outer peripheral surface of the recess 22 such that the recess rim 23 and the support surface 24 are engaged with the protruding rim 34, so that surface tension is increased due to a double-engagement, thereby enhancing a waterproof function.

As described above, the cover plate 36 simultaneously presses the rubber pad 31 and the pressing part 32 such that the rubber pad 31 and the pressing part 32 are fixedly coupled to each other, thereby facilitating the operation of the keypad 30.

In this case, the cover plate 36 is provided with a transparent window section to cover a liquid crystal display screen, which is exposed through a window of the cover 20.

In addition, in order to couple the body 10 with the cover 20, the body 10 has a stepped protrusion 18 formed at an outer peripheral portion of an upper rim thereof, and the cover 20 has a packing groove rim 26 for surrounding a protruding rim 19 defined by the stepped protrusion 18. The protruding rim 19 is pressed in a state in which a packing 60 is embedded in the packing groove rim, an outer rim 27 of the cover 20 is placed on the stepped protrusion 18, and an inner rim 28 of the cover 20 makes contact with an inner wall of the body 10.

Accordingly, the waterproof function can be obtained as the packing 60 is pressed through the engagement. In addition, the outer rim 27 and the inner rim 28 adhere to the stepped protrusion 18 and the inner surface of the body 10, respectively, so that surface tension is increased and airtight state is ensured due to the packing 60, thereby enhancing a water-proof function.

In this state, the coupling protrusions 15 and 21 are coupled with each other at a rear side of the body 10 and then a screw is used to fasten the cover 20 and the body 10, so that the cover 20 is tightly coupled with the body 10.

In this case, the screw has a packing installed on a head portion thereof, thereby maintaining the airtight state.

In addition, the syringe receptacle 12 and the battery receptacle 11 have a cap 70, which is open/closed through a screw mechanism, at an upper portion thereof. In order to fasten the cap 70 with a predetermined fastening force, an entrance part 10b and an inclined guide groove 10c are formed on a cap-coupling part 10a of the body 10, and a stopper 10d is formed at one end of the inclined guide groove 10c. Therefore, a guide protrusion 71 formed on the cap 70 is introduced into the entrance part 10b and then moves along the inclined guide groove 10c to make contact with the stopper while providing a predetermined pressing force. Accordingly, the cap-coupling part 10a is prevented from being damaged even if a strong fastening force is applied thereto.

The cap 70 is provided with a packing 72 to ensure the waterproof function.

Mode for the Invention

Accordingly, the piston 52 is removed from the cylinder 50 in a state in which medical fluid has been injected into the cylinder 50 so that only the packing part 51 is installed in the cylinder. In this state, the cylinder 50 of the syringe is inserted into the syringe receptacle 12 of the body 10 and passes through a perforation part 13 of the syringe receptacle 12 such that the guide groove 14 is coupled with the guide wing 43 of the movable shaft 42. In this state, the gear box 40 operates, so that the rotating shaft 41 rotates, thereby allowing the movable shaft 42 to be rotated. The guide wing 43 is embedded into the embedded part 53 of the packing part 51 installed on the cylinder 50, so the packing part 51 inserted into the cylinder 50 is pushed upward and the movable shaft 42 makes a precise vertical movement without fluctuation in the cylinder 50. In addition, since the engagement part 44 of the gear box 40 is fixed to the stopper 17 of the body 10, the movable shaft 42 makes a precise vertical movement without fluctuation when the motor 45 operates.

In addition, the body 10 and the cover 20, which form the case, are screw-fastened to be open/closed by means of two-step engagement and the packing 60, thereby facilitating the replacing work and repairing work of components installed in the body 10. The assembling work of the case is performed in a completely open field, thereby facilitating the assembling work. The stopper 17 is securely fixed to the engagement part 44, so that the movable shaft 42 is prevented from being fluctuated during the operation of the motor 45, thereby enabling the movable shaft 42 to make a precise vertical movement.

INDUSTRIAL APPLICABILITY

The delivery apparatus for medical fluid according to the present invention enables insulin to be regularly injected into a diabetic patient and is suitable for the patient who needs to take a shower or exercise in a state in which a syringe is inserted into a body.

SEQUENCE LISTING diabetic patient, insulin, automatic injector

The invention claimed is:

1. A delivery apparatus for medical fluid fabricated in a box type with a syringe, the delivery apparatus comprising:
a case including a body, an upper portion of which is open and in which a battery receptacle and a syringe receptacle are integrally formed;
a gear box driven by a motor and including a rotating shaft for rotatably engaging with a moveable shaft is introduced into and withdrawn from a syringe receptacle;
a cover with a recess;
a keypad for controlling an operation of the moveable shaft is installed in the recess of the cover and is fixed by a pressing part and a cover plate, and the cover and the body are screw-fastened in a state in which coupling protrusions and thereof are engaged with each other such that the cover is detachably coupled with the body;
a protruding rim having a flange formed at an edge of a rubber pad covering a substrate of the keypad received in the recess; and
a recess rim and a support surface formed on an outer peripheral surface of the recess such that the recess rim and support surface are engaged with the protruding rim, thereby increasing surface tension due to a double-engagement and enhancing a water-proof function,
wherein the gear box has a supporting guide formed on the body making contact with the gear box to prevent vibration caused by a rotation of the motor from being transferred into the moveable shaft, and wherein a predetermined gap is formed between the gear box and the body to absorb vibration in a case where the gear box comes close to contacting the body.

2. The delivery apparatus of claim 1, further comprising:
a stopper formed at a lower portion of the body forming the case such that the stopper is engaged with an engagement part of the gear box having the movable shaft which allows a packing part of a cylinder of the syringe, which is housed in the syringe receptacle, to precisely perform a vertical movement, so that the movable shaft is prevented from being fluctuated when the motor operates and when the rotating shaft protruding through the engagement part rotates.

3. The delivery apparatus of claim 1, wherein the movable shaft has a guide wing screw-coupled to the rotating shaft, and the movable shaft is engaged with a perforation part and a guide groove of the syringe receptacle, so that only the movable shaft makes a precise vertical movement when the rotating shaft rotates.

4. The delivery apparatus of claim 1, wherein only the packing part prepared in the cylinder makes up/down movements in a state in which the movable shaft is inserted into the cylinder of the syringe and the guide wing of the movable shaft is coupled to an embedded part of the packing part.

5. The delivery apparatus of claim 1, wherein the delivery apparatus can perform a waterproof treatment relative to a key pad for operating the motor of the gear box, the deliver apparatus further comprising:
a connecting hole formed in the recess for a signal connection with the substrate of the key pad,
wherein, the recess has a predetermined depth that is deep enough to receive the key pad.

6. The delivery apparatus of claim 1, wherein coupling the body with the cover comprises:
a stepped protrusion formed at an outer peripheral portion of an upper rim of the body;
a packing groove rim formed on the cover for surrounding a protruding rim defined by the stepped protrusion, wherein the protruding rim is pressed in a state in which a packing is embedded in the packing groove rim;
an outer rim of the cover on the stepped protrusion; and
an inner rim of the cover making contact between an inner wall of the body.

7. The delivery apparatus of claim 1, wherein, fastening the cap with a predetermined fastening force comprises:
an entrance part and an inclined guide groove formed on a cap-coupling part of the body;
a stopper formed at one end of the inclined guide groove, wherein a guide protrusion formed on the cap is introduced into the entrance part which moves along the inclined guide groove to make contact with the stopper while providing a predetermined pressing force, thereby preventing the cap-coupling part of the body from being damaged.

* * * * *